(12) United States Patent  (10) Patent No.: US 7,753,863 B2
Richard  (45) Date of Patent: Jul. 13, 2010

(54) NON INVASIVE EXTERNAL LIMB STABILIZER

(76) Inventor: Patricia Richard, 110 Sturges Hwy., Westport, CT (US) 06880

( * ) Notice: Subject to any disclaimer, the term of this patent is extended or adjusted under 35 U.S.C. 154(b) by 441 days.

(21) Appl. No.: 11/170,918

(22) Filed: Jun. 30, 2005

(65) Prior Publication Data

US 2007/0000500 A1  Jan. 4, 2007

(51) Int. Cl.
A61F 5/00  (2006.01)

(52) U.S. Cl. .......................... 602/23; 602/5

(58) Field of Classification Search ............ 602/23, 602/28, 29
See application file for complete search history.

(56) References Cited

U.S. PATENT DOCUMENTS

| | | | |
|---|---|---|---|
| 570,085 A | 10/1896 | Clausson | |
| 1,429,776 A | 9/1922 | Robinson | |
| 2,522,887 A | 9/1950 | Nelson | 155/165 |
| 2,697,436 A | 12/1954 | Coston | 128/214 |
| 2,709,435 A | 5/1955 | Kress | 128/260 |
| 2,732,269 A | 1/1956 | Astroff | 311/11 |
| 2,744,526 A | 5/1956 | Saylors | 128/214 |
| 2,850,342 A | 9/1958 | Robinson | 311/10 |
| 3,027,895 A | 4/1962 | Williams | 128/133 |
| 3,044,797 A | 7/1962 | Borland | 280/87.02 |
| 3,482,566 A | 12/1969 | Watkins | 128/133 |
| 3,803,954 A * | 4/1974 | Lenker | 81/126 |
| 3,901,228 A | 8/1975 | Brown | 128/133 |
| 3,981,030 A | 9/1976 | Turner | 5/327 |
| 4,023,568 A | 5/1977 | Murphy | 128/83 |
| 4,090,268 A | 5/1978 | Turner | 5/327 |
| 4,169,468 A | 10/1979 | Murphy | 128/83 |
| 4,181,297 A | 1/1980 | Nichols | 269/328 |
| 4,186,738 A | 2/1980 | Schleicher et al. | 128/153 |
| 4,275,472 A | 6/1981 | Erck | 5/60 |
| 4,299,213 A | 11/1981 | Violet | 128/133 |
| 4,344,339 A * | 8/1982 | Penner | 81/157 |
| 4,373,709 A | 2/1983 | Whitt | 269/328 |
| 4,407,277 A | 10/1983 | Ellison | 128/82 |
| 4,428,571 A | 1/1984 | Sugarman | 269/328 |
| 4,580,468 A * | 4/1986 | Cox | 81/138 |
| 4,647,028 A | 3/1987 | Yang | 269/139 |
| 4,809,687 A | 3/1989 | Allen | 128/84 |
| 4,831,903 A * | 5/1989 | Dausey et al. | 81/165 |
| 4,996,977 A | 3/1991 | Tiedeken | 128/77 |
| 5,042,508 A | 8/1991 | Richard | 128/882 |
| 5,944,677 A | 8/1999 | Richard | 602/23 |

* cited by examiner

Primary Examiner—Patricia M Bianco
Assistant Examiner—Camtu T Nguyen
(74) Attorney, Agent, or Firm—Perman & Green, LLP

(57) ABSTRACT

A limb stabilizing device includes a base, a first clamping member adjustably mounted to the base, and a second clamping member mounted in an opposed relationship with the first clamping member. The first clamping member includes a first adjustment mechanism that operates to allow the first clamping member to slide laterally along the base and to maintain the first and second clamping members in lateral alignment.

5 Claims, 9 Drawing Sheets

NON INVASIVE EXTERNAL LIMB STABILIZER

This invention relates to limb positioning devices and in particular to external devices that prevent or limit limb movement.

BACKGROUND

U.S. Pat. No. 6,793,655 discloses an invasive external fixation device that extends through the skin to engage a patient's bones with a number of pins and clamps supported by a rod. Care must be taken with this type of fixation device to treat bacteria penetrating the patient's skin and bones because the pins passing through the skin act as a conduit for bacteria. Antibiotics have to be administered as bacteria may enter the blood, bones, and soft tissues, and resistant strains may develop.

U.S. Pat. No. 5,042,508 is directed to a unitary arcuate limb engaging element with an integral base. Portions of the limb engaging element are forced apart to receive a portion of a limb and then return to their original shape to grip the limb. The integral base provides a wide transverse support for bracing the limb engaging element when the device is in operation. However, the limb engaging element is not adjustable over a wide range of limb diameters.

U.S. Pat. No. 5,944,677 describes dual limb immobilizers, each having a pair of upwardly extending limb embracing elements that are laterally adjustable. The dual immobilizers are longitudinally adjustable between themselves. While the limb embracing elements are adjustable, the adjustments are not particularly easy to make and are not easily repeatable. In addition, it may be particularly difficult for a patient to make adjustments while using the immobilizers.

It would be advantageous to provide a limb stabilizer that is non-invasive and thus does not contribute to the risk of introducing infection. It would also be desirable to provide a limb stabilizer that is easily and repeatably adjustable by a patient when using the device.

SUMMARY OF THE EXEMPLARY EMBODIMENTS

The exemplary embodiments are directed to a limb stabilizer that includes a pair of stabilizing devices having a base, a first clamping member adjustably mounted to the base, and a second clamping member fixed to the base in an opposed relationship with the first clamping member. The first clamping member includes an adjustment mechanism that operates to allow the first clamping member to slide laterally along the base and maintain the first clamping member in lateral alignment with the base and the second clamping member. The limb stabilizer includes one or more spacing members attached between the bases of the pair of stabilizing devices for maintaining a distance along a limb between the two limb stabilizing devices.

BRIEF DESCRIPTION OF THE DRAWINGS

The foregoing aspects and other features of the present invention are explained in the following description, taken in connection with the accompanying drawings, wherein.

DETAILED DESCRIPTION OF THE EXEMPLARY EMBODIMENTS

Figure 1A:
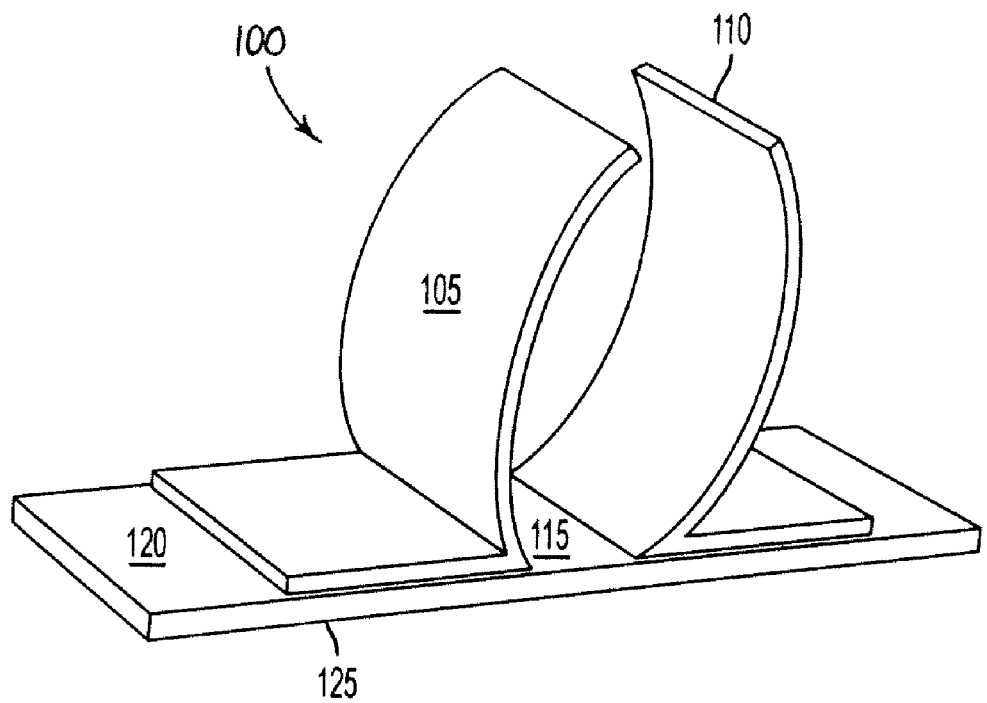
FIG. 1A shows a stabilizing device according to the disclosed embodiments.

FIG. 1A shows a stabilizing device 100 according to the embodiments disclosed herein. Although the exemplary embodiments will be described with reference to the drawings, it should be understood that the embodiments can include many alternate forms. In addition, any suitable size, shape or type of elements or materials could be used to implement the embodiments.

The stabilizing device 100 includes at least a pair of opposed clamping members 105, 110 mounted on a base 115. The clamping members 105, 110 are movable to embrace a patient's limb, for example, an arm or leg. The base 115, and clamping members 105, 110 operate to stabilize the limb during rehabilitation. In addition, the stabilizing device 100 is adapted to be positioned laterally with respect to another stabilizing device, thus positioning one limb with respect to another.

The base 115 generally extends laterally from the patient's limb and may have an upper surface 120 and a lower surface 125. The base may have a height 130 that elevates the limb. The lower surface 125 may be coated, patterned, or otherwise formed to prevent slippage. In one embodiment, a material may be applied or a pad may be fastened to the lower surface 125 to retard any movement of the base 115 when in contact with another surface. The upper surface 120 may be generally flat.

Figure 1B:
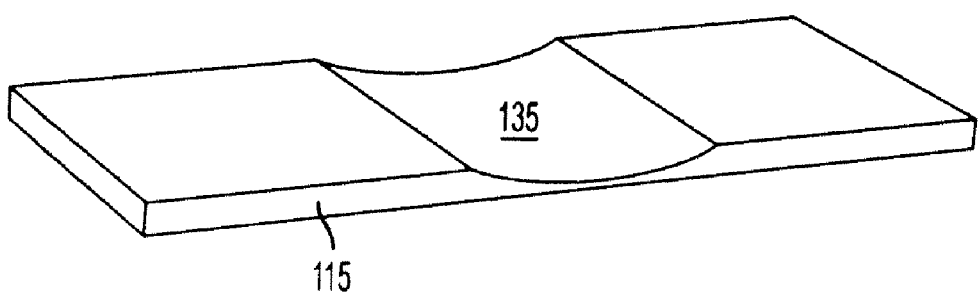
FIG. 1B shows an embodiment of a base for the stabilizing device.

In another embodiment shown in FIG. 1B, the upper surface may have a central concavity 135 to mold to the limb or in which the limb may rest. The upper surface and may include various mounting points and guides for the clamping members 105, 110, other devices for fastening and adjusting the clamping members 105, 110, and other mechanisms for locating the stabilizing device 100 with respect to another stabilizing device. At least two clamping members 105, 110 may be mounted to the upper surface 120 of the base 115 in an opposed relationship. The base may be constructed of metal, wood, or any other suitable material. In one embodiment, the base may be made of a plastic material.

Figure 2:
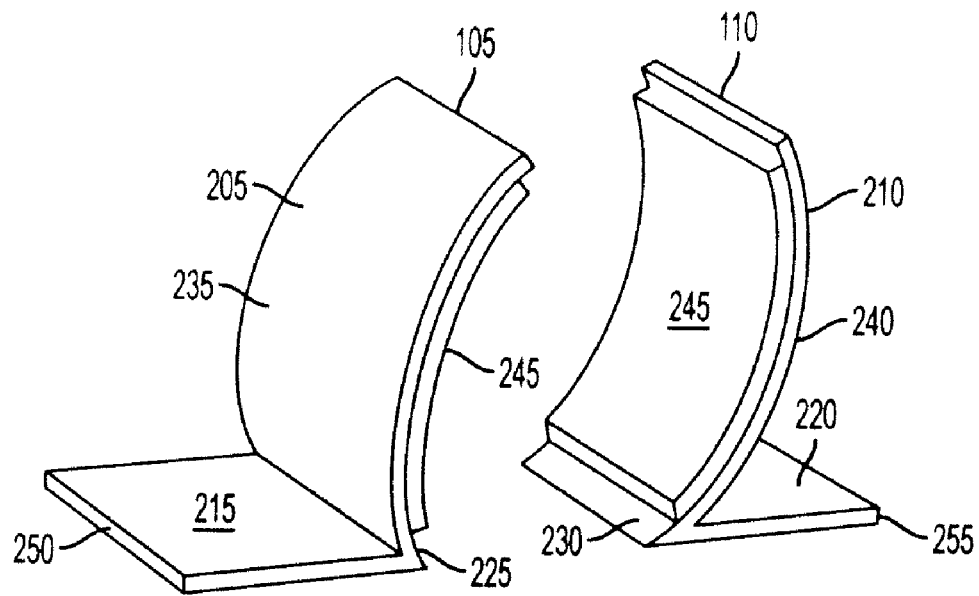
FIG. 2 depicts a detailed view of clamping members used in the stabilizing device.

Referring to FIG. 2, the clamping members 105, 110 may each include a support arm 205, 210 and a base plate 215, 220. In one embodiment, each support arm 205, 210 may be identical in construction, except that one may generally be the mirror image of the other. Each support arm 205, 210 may have a generally semi-circular, curved, or arcuate shape with an inwardly facing side 225, 230 and an outwardly facing side 235, 240. The inwardly facing side 225, 230 of each support arm 205 210 may include an opposing concave surface. Padding or cushioning material 245 may be attached to the inwardly facing side. The height of the support arms 205, 210 may be ample enough to enclose the limb sufficiently to stabilize the limb and to prevent unwanted movement.

The base plate 215, 220 of each clamping member 105, 110 includes an outwardly extending foot 250, 255 which contacts the base 115. Each foot may generally include mechanisms for interfacing with the mounting points, guides, fastening and adjusting devices, and other locating mechanisms on the upper surface 120 of the base 115.

Similar to the base 115, the clamping members 105, 110 may be constructed of a suitable material, for example, metal or wood. The clamping members 105, 110 may also be made from a plastic material suitable for implementing the features described herein.

Figure 3:
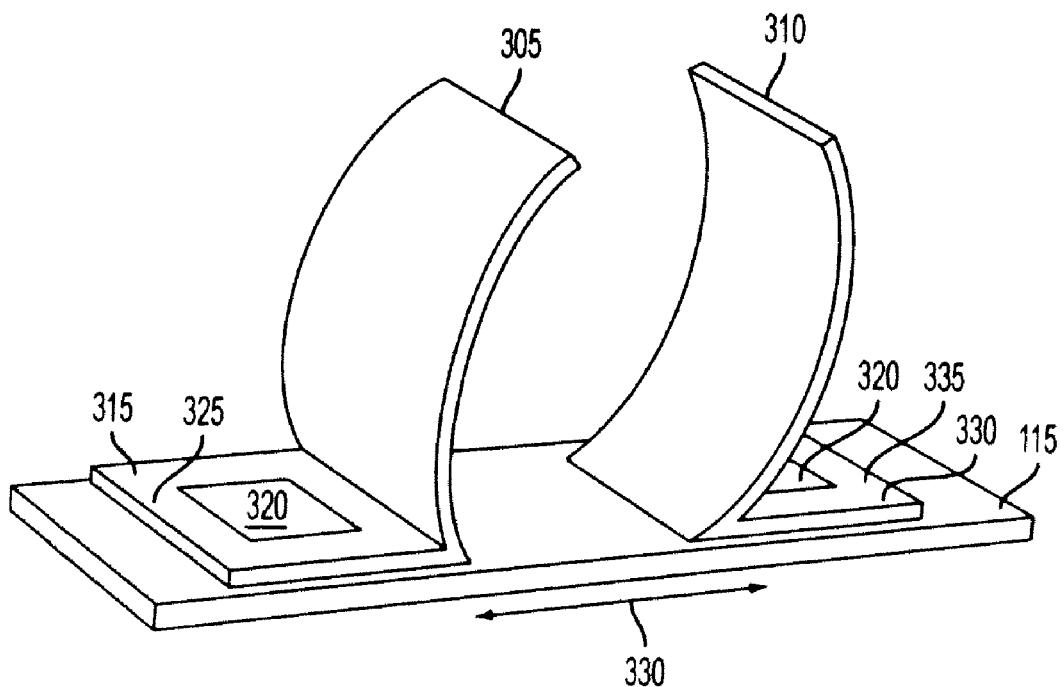
FIG. 3 portrays a perspective view of an embodiment of a stabilizing device.

FIG. 3 shows a perspective view of one embodiment of an exemplary stabilizing device 300 with first and second clamping members 305, 310. First clamping member 305 includes a footplate 315 with an upper surface 325. Footplate 315 may also include an adjustment mechanism 320 that allows lateral movement as shown by arrow 330 of the first clamping member 305. Similarly, second clamping member 310 may also include a footplate 330 with an upper surface 335 and an adjustment mechanism 320.

In another embodiment, second clamping member 310 has no adjustment mechanism and is rigidly fixed to, or integral with, the base 115.

Figure 4:
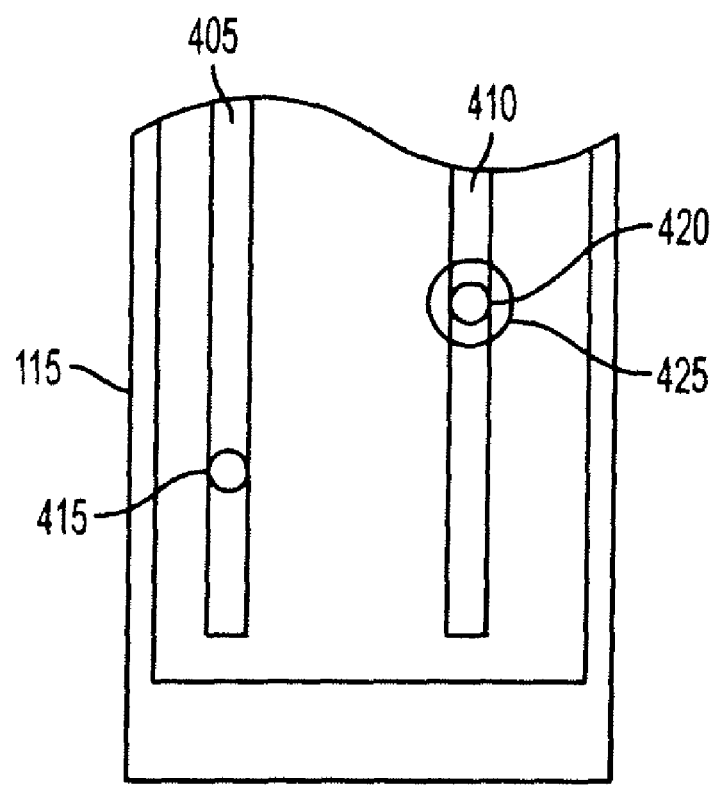
FIG. 4 illustrates an exemplary adjustment mechanism.

One embodiment of the adjustment mechanism 320 is shown schematically in FIG. 4. The adjustment mechanism 320 includes at least first and second slots 405, 410. A guide pin 415 integral to or fastened to the base 115 extends upward through first slot 405 and may slidingly engage the sides of the first slot 405. In one embodiment guide pin 415 may not extend past the upper surface 325 of footplate 315.

A stud 420 is integral to or fastened to the base 115 and extends upward through slot 410. A fastener 425 is attached to stud 425 such that in a loosened state the fastener 425 allows the first clamping member 305 to slide longitudinally along the base 115. In a tightened state the fastener 425 operates to hold the first clamping member 305 in a fixed position.

The first and second slots 405, 410 in combination with guide pin 415 and stud 420 serve to allow first clamping member 305 to slide laterally along the base 115 and maintain first clamping member 305 in lateral alignment, with the base 115 and second clamping member 310. In operation, the fastener 425 is loosened, the first clamping member 305 is placed in a desired position, and the fastener is tightened to fix the first clamping member 305 in the desired position.

Figure 5:
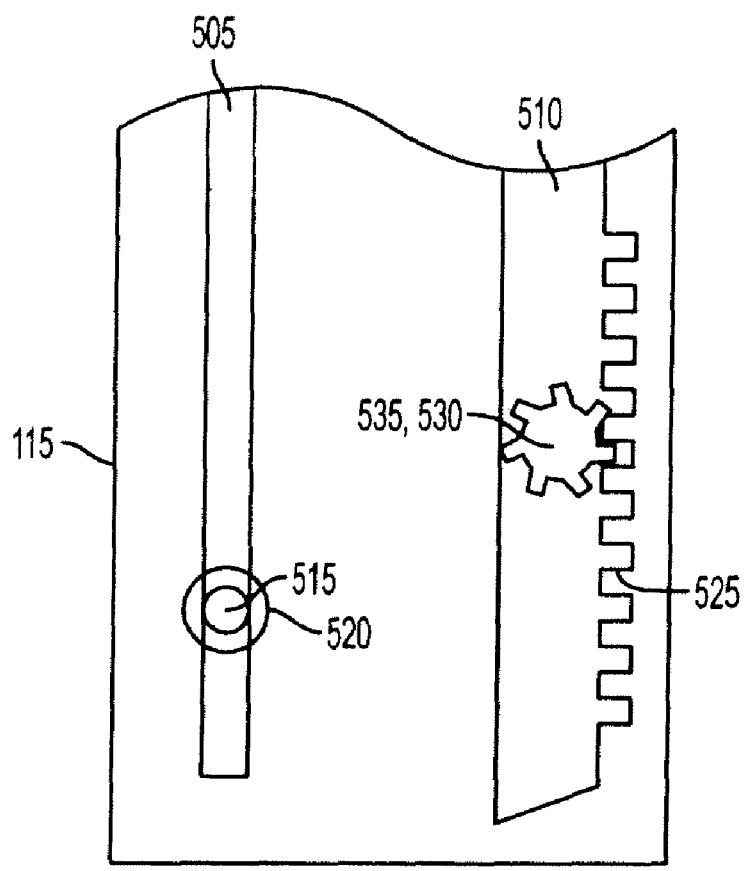
FIG. 5 shows another exemplary adjustment mechanism.

Another embodiment of the adjustment mechanism 320 is schematically shown in FIG. 5. In this embodiment, the adjustment mechanism 320 includes at least first and second slots 505, 510 and a first stud 515 integral to or fastened to the base 115. The first stud 515 extends upward through and may slidingly engage the sides of first slot 505. A fastener 520 is attached to first stud 515 such that in a loosened state the fastener 520 allows the first clamping member 305 to slide laterally along the base 115. In a tightened state the fastener 520 operates to hold the first clamping member 305 in a fixed position. Slot 510 includes a rack 525. A second stud 530 is integral to or fastened to the base 115 and extends upward through slot 510. A pinion 535 is attached to stud 530 so as to rotatably engage the rack 525.

The first and second slots 505, 510 in combination with first stud 515, rack 525, and pinion 535 operate to allow first clamping member 305 to slide laterally along the base 115, while at the same time maintaining first clamping member 305 in lateral alignment with the base 115 and second clamping member 310. The fastener 520 may be loosened and the pinion 535 may be rotated to cause the engaged rack 525, and thus first clamping member 305, to slide laterally along the base 115. Upon reaching a desired position, the fastener 520 may be tightened to fix the first clamping member 305 in position.

Figure 6:
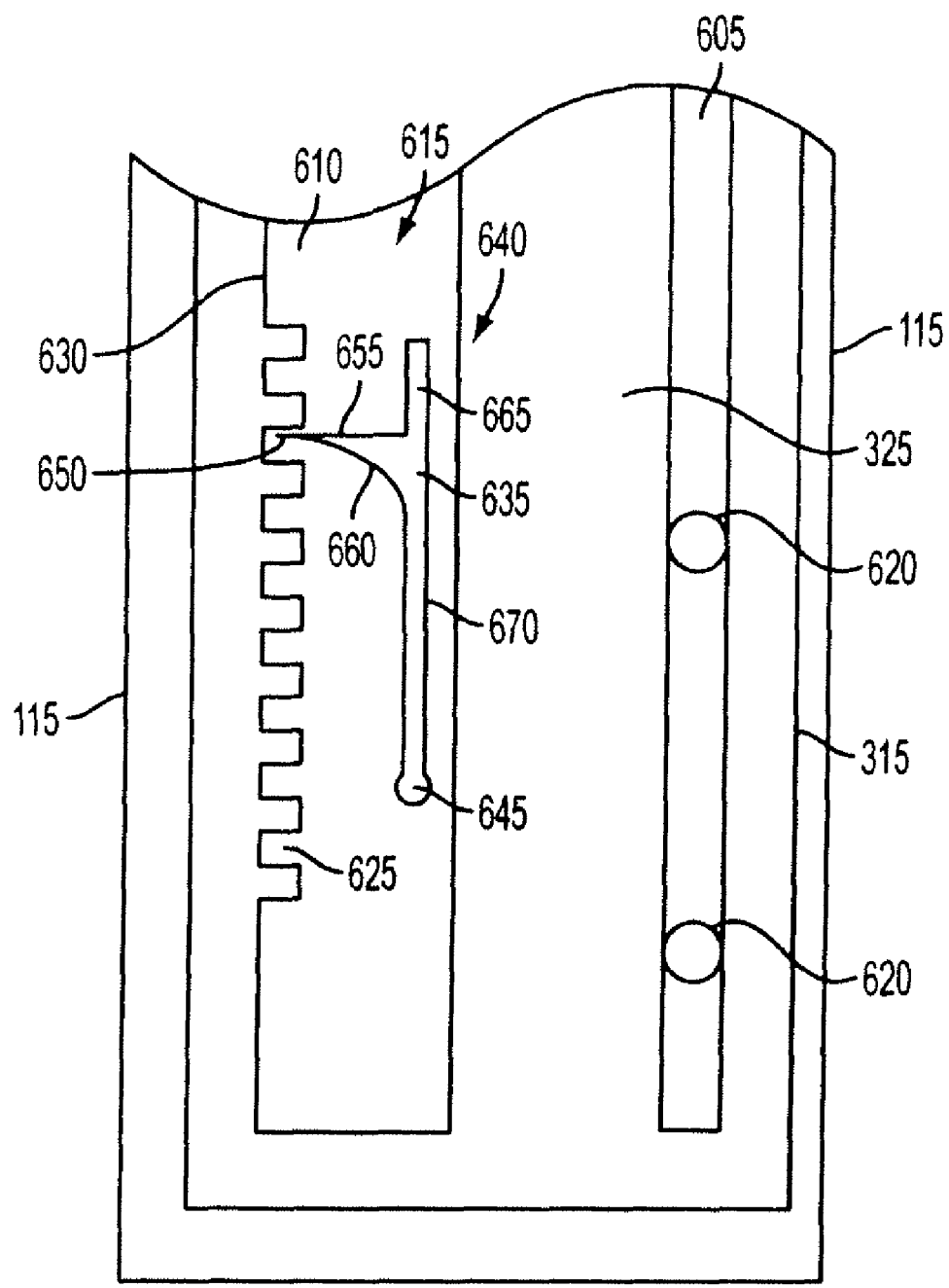
FIG. 6 depicts yet another exemplary adjustment mechanism.

Yet another embodiment of the adjustment mechanism 320 is shown schematically in FIG. 6. In this embodiment, the adjustment mechanism 320 includes at least first and second slots 605, 610 and a ratcheting mechanism 615.

One or more guide pins 620 integral to or fastened to the base 115 may extend upward through first slot 605 and may slidingly engage the sides of the first slot 605. In one embodiment, guide pins 620 may not extend past the upper surface 325 of footplate 315. In an embodiment utilizing more than one guide pin 620, the more than one guide pins 620 in combination with the first slot 605 function to guide first clamping member 305 laterally along the base 115 and to maintain the first clamping member 305 in lateral alignment with the base 115 and second clamping member 310.

The ratcheting mechanism may include a plurality of spaced grooves 625 set in one wall 630 of second slot 610 and a detent 635. The detent is adapted to be situated in grooves 625 to fix the position of the first clamping member 305. The detent 635 may generally include a free end 640 and a fixed end 645. The free end 640 may include a tip 650, a flat surface 655, a curved surface 660, a release tab 665, and a biasing mechanism 670. The fixed end may be fixedly pinned to the base 115.

The tip 650 may be formed at the intersection between the flat surface 655 and the curved surface 660 and is positioned to engage the grooves 625. The flat surface 655 operates to hold the first clamping member 305 in place, while the curved surface 660 allows movement of the first clamping member 305 in one direction. The release tab 665 provides a lever that permits the tip 650 to be moved out of engagement with the grooves 625. This may allow free movement of the first clamping member 305 as guided by the more than one pins 620 in combination with the first slot 605. The biasing mechanism 670 may include a segment of the detent acting as a spring to bias the tip 650 toward the grooves 625.

To adjust the stabilizing device in this embodiment, the first clamping member 305 may be urged toward the second clamping member 310. The curved surface 660 and biasing mechanism 670 allows the plurality of spaced grooves 625 to pass the tip 650 until the desired position of the first clamping member 305 is achieved. The tip then engages the grooves 625 along with the flat surface 655 to maintain the desired position. The release tab 665 may be used to disengage the tip to release the first clamping member 305.

Figure 7A:
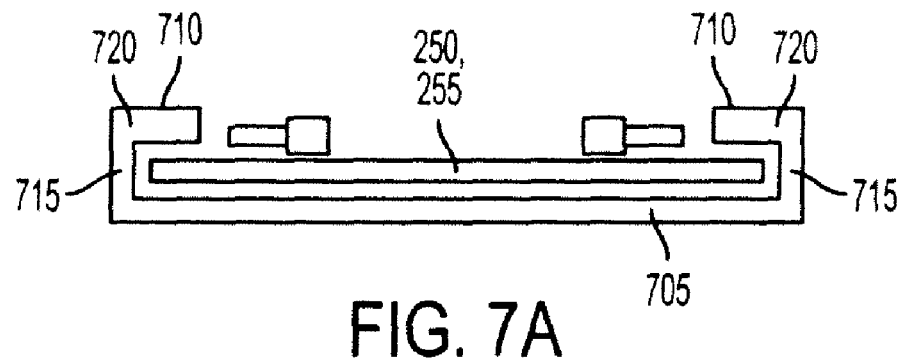
FIG. 7 depicts still another exemplary adjustment mechanism.
Figure 7B:
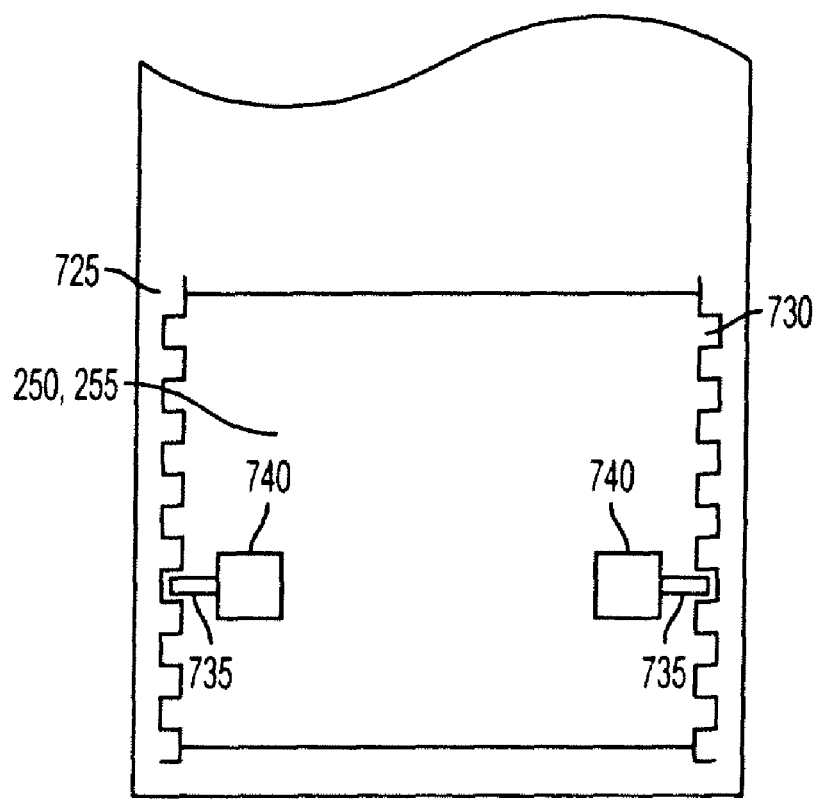

Still another embodiment of the adjustment mechanism 320 that includes a ratcheting mechanism is schematically shown in FIGS. 7A and 7B. Referring to FIG. 7A, the base 705 of the stabilizing device includes rails 710 that extend laterally. The rails 710 are formed such that the outwardly extending foot 250, 255 of each clamping member 305, 310 is captured and guided by the rails, allowing each foot 250, 255 to slide laterally while maintaining the first clamping member 305 and the second clamping member 310 in lateral alignment with each other. Each of the rails 710 include an upwardly extending portion 715 and an inwardly extending portion 720.

Referring to FIG. 7B, each of the inwardly extending portions 720 of rails 710 include a rack 725 having a series of equally spaced indentations 730. A plurality of pins 735, each having a biasing mechanism 740 are mounted on the outwardly extending foot 250, 255 and are biased to engage the equally spaced indentations 730. Thus, the racks 725, pins 735, and biasing mechanisms 740 form a ratcheting mechanism. In operation, the pins 735 are retracted and the outwardly extending foot 250, 255 of the clamping member 305, 310 is allowed to slide laterally to a desired adjusted position. Once in position, the pins are allowed to return to their biased position to secure the clamping member in place.

It should be understood that the ratcheting mechanism adjustment embodiments shown in FIGS. 7A and 7B may be implemented on one of the outwardly extending feet 250, 255 of the clamping members 305, 310 while the other clamping member may be fixed to the base 705.

It should be noted that the embodiments of the adjustment mechanism 320 as described herein provide a repeatable adjustment of the first clamping member 305 with respect to the second clamping member 310. Furthermore, embodiments where the second clamping member 310 as fixed or integral to the base 115 are advantageous because an adjustment is only required for the first clamping member 305 as opposed to both the first and second clamping members 305, 310, simplifying and reducing the effort of the adjustment process.

Figure 8:
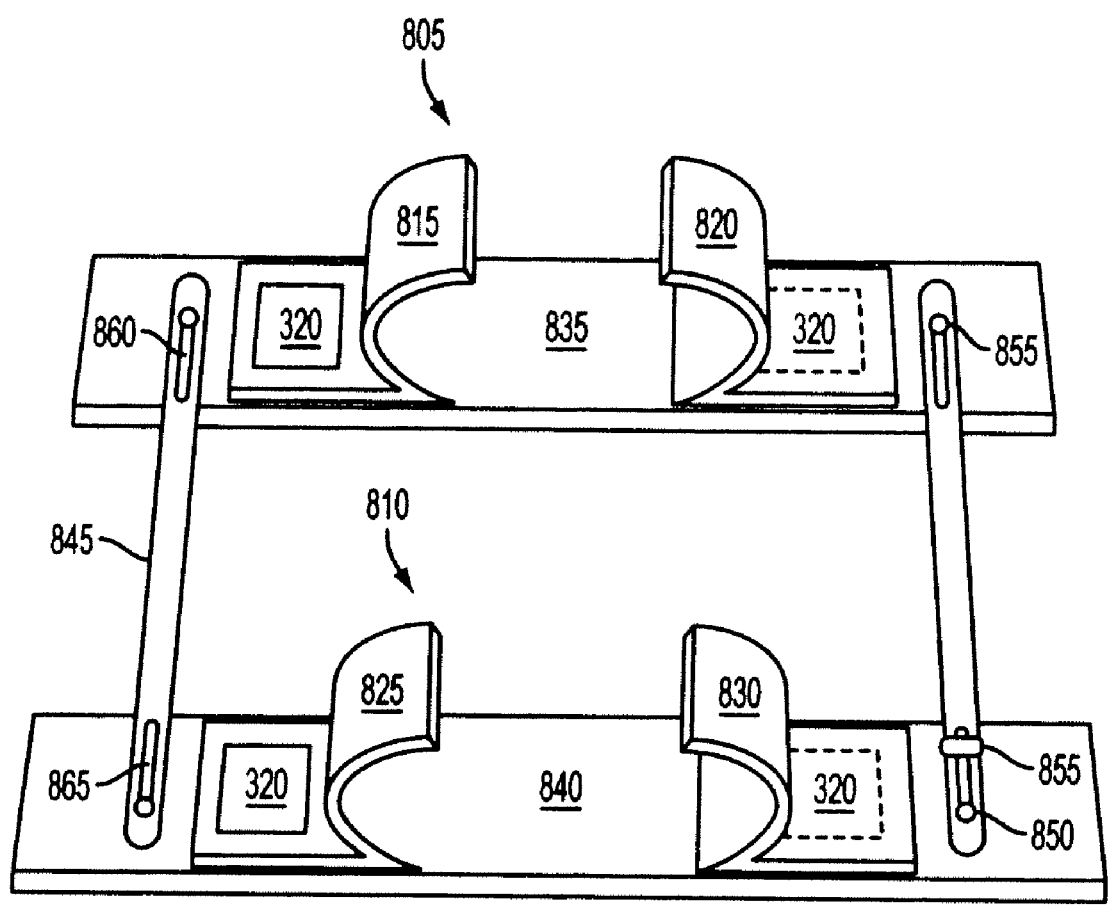
FIG. 8 portrays an embodiment with two stabilizing devices.

FIG. 8 shows another embodiment utilizing dual stabilizing devices 805, 810 having bases connected by one or more spacing members 845. Each stabilizing device 805, 810 includes first and second opposed clamping members 815, 820 and 825, 830, respectively. First and second opposed clamping members 815, 820 are mounted on a base 835, and first and second opposed clamping members 825, 830 are mounted on a base 840. Each first opposed clamping member 815, 825 may be adjustable with respect to its second opposed clamping member 820, 830. For example, each first opposed clamping member 815, 825 may include the adjustment mechanisms 320 as embodied in FIGS. 4, 5, 6, and 7A and 7B. In one embodiment, each second opposed clamping member 825, 830 may also include the adjustment mechanism 320 that allows lateral adjustment.

In another embodiment, each second opposed clamping member 820, 830 may be rigidly fixed to, or integral with its respective base 835,840.

In this embodiment, the first and second stabilizing devices 805, 810 may be arranged along the length of a patient's limb and are attached by the one or more spacing members 845. The spacing members may be rigidly constructed of wood, metal, plastic, or any other suitable material. In an exemplary embodiment, studs 850 may protrude from the base 835 of first stabilizing device 805 and the base 840 of the second stabilizing device 710 to receive and engage slots 860,865 in each of the spacing members 845. A fastener 855 may engage each stud 850 and operate to clamp the spacing members 845 to the stabilizing device bases 835, 840 to maintain the first and second stabilizing devices 805, 810 at a desired distance from each other. The slots 860, 865 may be elongated to provide a desired distance variation.

The one or more spacing members 845 attached to the bases 835, 840 advantageously provide a stable, rigid connection between stabilizing devices 805, 810 that is independent of the sets of first and second opposed clamping members 815, 820 and 825, 830. The spacing members 845 also provide a connection without interfering with the operation of the sets of first and second opposed clamping members 815, 820 and 825, 830.

Figure 9:
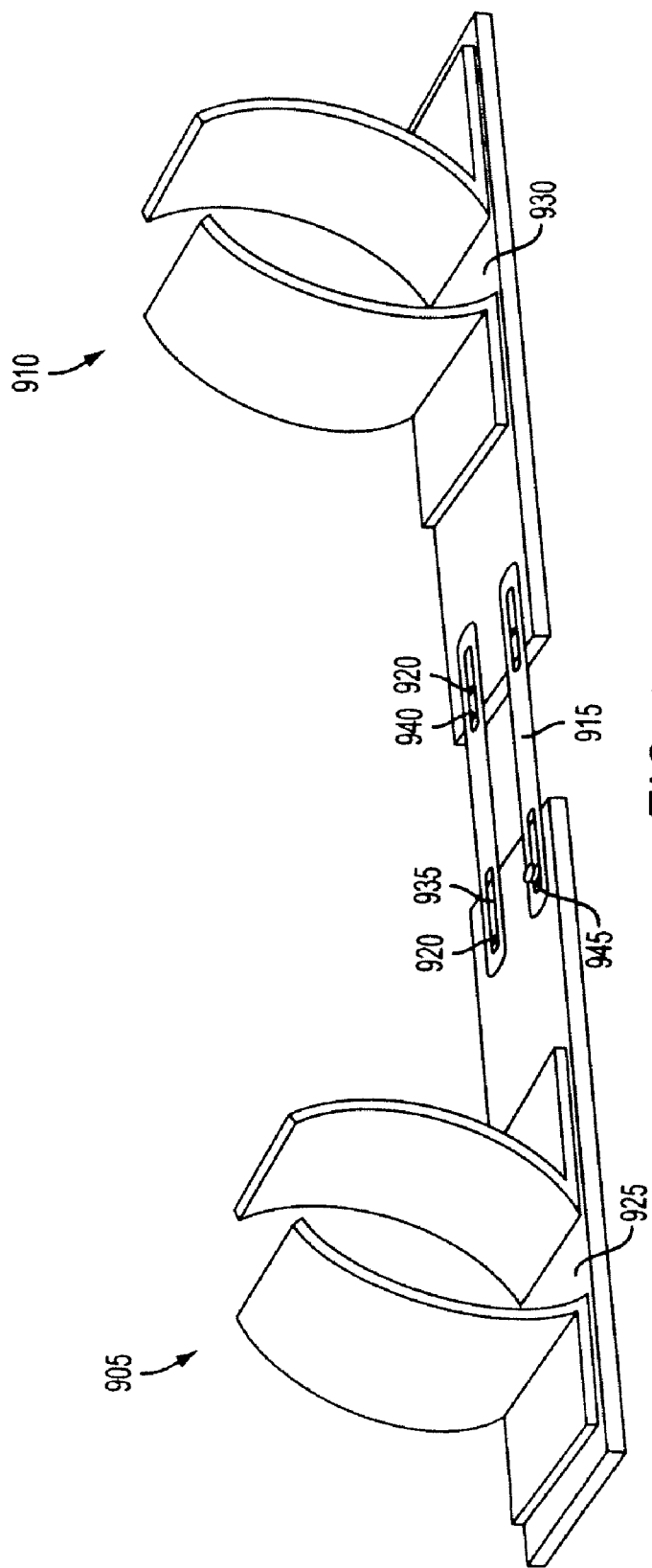
FIG. 9 portrays another embodiment with two stabilizing devices.

FIG. 9 shows yet another embodiment for stabilizing one limb with respect to another limb. In this embodiment, a first and second stabilizing device 905, 910 are attached by one or more spacing members 915, which may be similar in construction to spacing members 845 (FIG. 8). In an exemplary embodiment, studs 920 may protrude from the base 925 of first stabilizing device 905 and the base 930 of the second stabilizing device 910 to receive and engage slots 935, 940 in each of the spacing members 915. A fastener 945 may engage each stud 920 and operate to clamp the spacing members 915 to the stabilizing device bases 925, 930 to maintain the first and second stabilizing devices 905, 910 at a desired lateral distance from each other. The slots 935, 940 may be elongated to provide a desired lateral distance variation.

Figure 10:
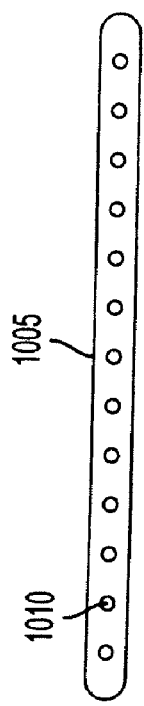
FIG. 10 illustrates an exemplary embodiment of spacing members.

In another embodiment shown in FIG. 10, the one or more spacing members 1005 may include a number of spaced holes 1010. The spaced holes 1010 may receive the studs and provide a desired distance variation the first and second stabilizing devices 805, 810 of the embodiment of FIG. 8 or the first and second stabilizing devices 905, 910 of the embodiment of FIG. 9.

Figure 11:
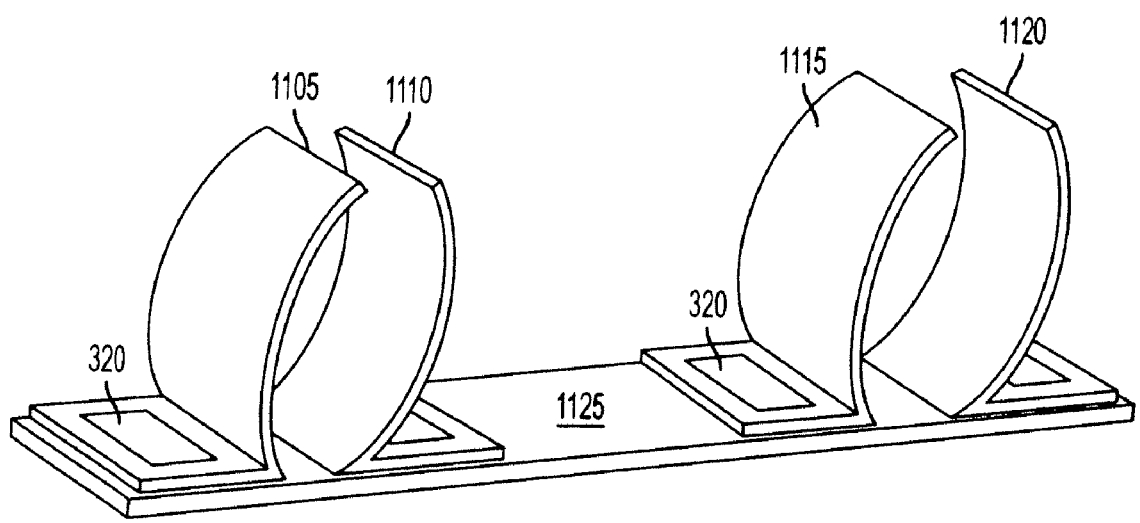
FIG. 11 illustrates yet another embodiment with two stabilizing devices.

FIG. 11 shows still another embodiment for stabilizing one limb with respect to another limb where the clamping members 1105, 1110, 1115, 1120 are mounted on a common base 1125. In one aspect of this embodiment each clamping member 1105, 1110, 1115, 1120 may include an adjustment mechanism 320 as described herein. In another aspect, the clamping members may be paired together, for example, clamping members 1105,1110 may be used to stabilize one limb and clamping members 1115,1120 may be used to stabilize another limb. In this other aspect, only one of each pair of clamping members may include an adjustment mechanism 320 and the other one of each pair may remain fixed to the base 1125.

Thus, the presently disclosed embodiments are advantageous because they provide pain relief through non-invasive limb stabilization without contributing to a risk of infection. The disclosed embodiments generally have no pins piercing the skin, blood vessels, nerves, or bones and thus does not induce pain in use, but rather, through non-invasive stabilization, provides pain relief. The disclosed embodiments provide such pain relief without the risk of osteomyelitis, and without the risk bacteria on the skin causing bone infection or entering the blood and causing bacteremia. In addition, there is less need for administering antibiotics and less of a risk that resistant strains will develop.

While particular embodiments have been described, various alternatives, modifications, variations, improvements, and substantial equivalents that are or may be presently unforeseen may arise to Applicant's or others skilled in the in the art. Accordingly, the appended claims as filed, and as they may be amended, are intended to embrace all such alternatives, modifications, variations, improvements and substantial equivalents.

What is claimed is:

1. A limb stabilizing device comprising:
    a base configured to extend laterally from the limb of a person, the base including an upper surface and an opposing bottom surface, the upper surface being configured to support the limb;
    a first clamping member adjustably mounted to the base; and
    a second clamping member integral with the base with no adjustment in an opposed relationship with the first clamping member, the first clamping member and second clamping member extending substantially perpendicularly from the upper surface of the base and being configured to effect clamping and stabilization of the limb of the person;
    wherein the first clamping member includes a first adjustment mechanism that operates to allow the first clamping member to slide laterally along the base and to maintain the first and second clamping members in lateral alignment.

2. The limb stabilizing device of claim 1, wherein the adjustment mechanism comprises a ratcheting assembly.

3. The limb stabilizing device of claim 2, wherein the ratcheting assembly includes:

one or more rails extending laterally along the base, each rail having a rack with a series of equally spaced indentations; and one or more pins, each having a biasing mechanism mounted on a foot of the first clamping member and each biased to engage the equally spaced indentations.

4. The limb stabilizing device of claim 1, wherein the base includes a first slot and a second slot, and the first adjustment mechanism comprises a guide pin that slidingly engages the first slot, a stud that engages the second slot, and a fastener that engages the stud and operates to clamp a foot piece of the first clamping member.

5. The limb stabilizing device of claim 1, wherein the first adjustment mechanism comprises:

a first slot and a second slot disposed in the base;

a guide pin that slidingly engages the first slot; and the second slot having a rack and pinion assembly.

* * * * *